(12) United States Patent
Kimura

(10) Patent No.: US 7,597,553 B2
(45) Date of Patent: Oct. 6, 2009

(54) ORTHODONTIC BRACKET

(76) Inventor: Norifumi Kimura, 124-14, Ooaza-Higashisue, Ube-shi (JP) 759-0206

( * ) Notice: Subject to any disclaimer, the term of this patent is extended or adjusted under 35 U.S.C. 154(b) by 0 days.

(21) Appl. No.: 11/604,779

(22) Filed: Nov. 28, 2006

(65) Prior Publication Data
US 2007/0128571 A1  Jun. 7, 2007

(30) Foreign Application Priority Data
Dec. 5, 2005  (JP) .............................. 2005-350078
May 17, 2006  (JP) .............................. 2006-137314

(51) Int. Cl.
*A61C 3/00* (2006.01)
(52) U.S. Cl. .................. 433/16; 433/8; 433/18
(58) Field of Classification Search ............... 433/8–17, 433/18–24
See application file for complete search history.

(56) References Cited
U.S. PATENT DOCUMENTS

| 3,421,221 | A | * | 1/1969 | Silverman et al. | 433/8 |
| 3,464,113 | A | * | 9/1969 | Silverman et al. | 433/11 |
| 4,197,642 | A | * | 4/1980 | Wallshein | 433/11 |
| 4,676,746 | A | * | 6/1987 | Klapper | 433/16 |
| 6,655,959 | B2 | * | 12/2003 | Farzin-Nia et al. | 433/18 |
| 2007/0009849 | A1 | * | 1/2007 | Wool | 433/10 |

FOREIGN PATENT DOCUMENTS

| JP | H08-112293 | 5/1996 |
| JP | 2005-185428 | 7/2005 |
| JP | 2005-192989 | 7/2005 |

* cited by examiner

*Primary Examiner*—John J Wilson
*Assistant Examiner*—Heidi M Eide
(74) *Attorney, Agent, or Firm*—Bacon & Thomas, PLLC

(57) ABSTRACT

An orthodontic bracket enables orthodontic treatment to be performed without resetting of a bracket body and an arch wire relative to the tooth, even in an advanced stage of the treatment. The orthodontic bracket comprises a bonding plate having a bonding surface matching the curvature of the tooth, a base having a bottom surface united with the bonding plate and an upper surface serving as a sliding surface parallel to the longitudinal axis of the tooth and taking an approximately rectangular shape in plan with a convex curve formed in accordance with the long axis of the tooth. A bracket body is mounted on the sliding surface of the base so as to be slidable along the tooth axis. The base has, at opposing sides of the sliding surface, grooved parallel rails for slidably holding the bracket body therebetween. Each rail has, at its opposite ends, stoppers to prevent detachment of the bracket body. The sliding surface has a central longitudinally-extending visible median line. The bracket body has, on its upper surface, wire slots arranged approximately orthogonal to the tooth axis.

5 Claims, 10 Drawing Sheets

ORTHODONTIC BRACKET

BACKGROUND OF THE INVENTION

1. Field of the Invention

This invention relates to an orthodontic bracket useful in correcting irregularities in alignment of teeth.

2. Description of the Related Arts

To treat patients troubled with irregularities in alignment of teeth, plural orthodontic brackets, made of metals and resins etc., are usually used. Each orthodontic bracket has a bracket body having, on its upper surface, wire slots adapted to hold an arch wire across the upper surface of the bracket body. Each orthodontic bracket is bonded with an adhesive to a surface (a front surface in the case of an incisor, or a side surface in the case of a molar) of each tooth to be repositioned.

For bonding each orthodontic bracket to a tooth side surface, the bracket position is set with respect to the tooth such that the bracket body's center line and the tooth center line are in alignment with each other and that the arch wire held with the wire slots of each orthodontic bracket is arranged linearly in parallel with a linear occlusal plane of the teeth to be obtained by orthodontic treatment. Then, each orthodontic bracket is bonded to set the bracket position for each tooth.

With the arch wire held in the wire slots of each orthodontic bracket placed on corresponding tooth side surfaces as described above, the orthodontic brackets are connected together through the arch wire. Then, insertion of the opposite ends of the arch wire into respective buccal tubes united with more distal teeth is performed with the arch wire under tension followed by connection of the arch wire to the respective buccal tubes.

With each orthodontic bracket placed on a corresponding tooth side surface as described the above, the orthodontic treatment is effected by the elastic recovery force of the arch wire to provide distal movement (movements from the incisor side toward the molars) or mesial movement (movement from the molar side toward the incisors) of each tooth requiring realignment, or alternatively, to adjust occlusion between upper and lower teeth and to eliminate torsion.

The orthodontic treatment may be applied after extraction of a tooth to eliminate crowding or without extraction. However, as is obvious from the above description, in either case, setting of the bracket position is quite important in order to bond each orthodontic bracket in proper position on a tooth.

Some important problems involved in bonding of each orthodontic bracket include positioning and/or orienting the bracket body so that the wire slot in the bracket body and the linear occlusal plane of teeth are parallel, positioning and/or orienting the bracket body for alignment between the bracket body and the corresponding tooth, and matching the contour of the bracket body to the corresponding tooth side surface.

To solve the above problems, Japanese Patent Laid-open No. 8-112293, for instance, discloses an orthodontic bracket having a bracket body having, at its opposite sides, a pair of tie-wings each having a central wire slot formed across it. Each tie-wing has a first visible reference line on its median, parallel to a longitudinal axis of the tooth, and each wire slot has, on its axis intersecting the first visible reference line, a second visible reference line parallel to a linear occlusal plane of the teeth. The orthodontic bracket of this type allows bonding to the corresponding tooth side surface with the adhesive using the first and the second visible reference lines, permitting the bracket to be bonded in its proper position in accordance with the longitudinal axis of each corresponding tooth and with the linear occlusal plane of the teeth.

Japanese Patent Laid-open Application No. 2005-192989 discloses an orthodontic bracket having a mark on a contour line extending from a longitudinal center line located on a bottom surface of each wire slot of the bracket body and defined by intersection of a plane perpendicular to the bottom surface of each wire slot with the surface of the bracket body. The orthodontic bracket of this type provides for alignment of the mark with a mid-transverse plane of the tooth to be bonded to the bracket and provides a bracket base point on the mid-transverse plane, thus locating the bracket accurately on the tooth.

However, the orthodontic bracket, even after accurate positioning of the each tooth brings about distal or mesial movements of the tooth to be corrected, with advance of the orthodontic treatment depending on clamping force of the arch wire, causes in a change in occlusion between the upper and lower teeth. Thus, the conventional orthodontic brackets cause a change in occlusion of the teeth with the advance of the orthodontic treatment, which change necessitates a change of bracket position setting. Thus frequently resetting of the bracket body of the arch wire is required, prolonging the time required for the orthodontic treatment, and imposing a heavy burden upon the patients.

SUMMARY OF THE INVENTION

The present invention differs from the conventional technology, in that it has as its object provision of an orthodontic bracket that enables orthodontic treatment to be performed without requiring resetting of the bracket body and the arch wire, even in an advanced stage of the orthodontic treatment.

To attain the above object, an orthodontic bracket according to the present invention comprises a bonding plate having a bonding surface matching a contour (curvature) of a tooth; a base having a bottom surface united with the bonding plate and an upper surface adapted to allow sliding parallel to the longitudinal axis of the tooth. The base has an approximately rectangular shape in plan view with a convex curvature extending along the longitudinal axis of the tooth; and a bracket body set on the sliding surface of the base in such a way that the bracket body may slide along the longitudinal axis of the tooth. The base has, on the opposite upper sections of the sliding surface, confronting groove-like parallel rails adapted to receive opposing portions of the bracket body slidably therein. Each rail has, at its opposite ends, stoppers to prevent detachment of the bracket body. The sliding surface has, at its widthwise center, a longitudinally-extending visible median line, and the bracket body has, on its upper surface, wire slots arranged approximately orthogonal to the longitudinal axis of the tooth.

In preparation for the orthodontic treatment with the orthodontic bracket according to the present invention, the bracket body is set on the sliding surface of the base by inserting the opposing portions of the bracket body in the respective rails of the base.

The above preparation is followed by adhesive-bonding of each base through the bonding plate to the side surface of respective teeth with each base held such that its median line is in alignment with the longitudinal axis of the tooth to which it is affixed and with each bracket body held such that the axis of each wire slot is arranged in parallel to a properly linear occlusal plane of the teeth to be obtained by the orthodontic treatment (or a normally linear occlusal plane).

Then, with the arch wire held in the wire slots of each bracket body, the bracket body is fastened to the base together with the arch wire with a fixture such as a ligature wire to prevent the bracket body from sliding along the sliding surface of the corresponding base. At the same time, the orthodontic brackets are interconnected.

Afterwards, the opposite ends of the arch wire are inserted into buccal tubes united with more distal teeth followed by connection of the arch wire to the buccal tubes to apply tension to the arch wire and also to press each bracket against each corresponding tooth. With this arrangement, the tooth requiring the orthodontic treatment gradually shifts toward its correct position.

When the orthodontic treatment of the tooth has advanced to a stage necessitating a change in set position of the bracket with respect to the tooth, repositioning of the bracket is performed by shifting the bracket body along the sliding surface of the base by a required distance parallel to the longitudinal axis of the tooth through a process of loosening or detaching the fixture such as the ligature wire, while loosening the arch wire. Then, with the repositioned bracket body re-fixed to the sliding surface of the base with the fixture such as the ligature wire to prevent sliding, and the opposite ends of the arch wire are reinserted into the respective buccal tubes followed by reconnection of the arch wire to the respective buccal tubes to reapply tension to the arch wire.

Thus, there is no need to reset the bracket body and/or the arch wire every time the orthodontic treatment has advanced to a stage necessitating a change in the set position of the bracket with respect to the tooth. Accordingly, the orthodontic bracket of the present invention enables the orthodontic treatment to be performed in a shorter period of time, and relieves the burden on the patent.

Further, the orthodontic bracket of the present invention has the base convex-curved in a shape in accordance with the tooth, permitting more successful matching of the convex-curved base to the tooth side surface and also permitting the installed posture of the bracket body, set on the sliding surface of the base, to better match the tooth side surface.

BRIEF DESCRIPTION OF THE DRAWINGS

The foregoing and other objects and features of the invention will become more apparent from the following description of preferred embodiments with reference to the accompany drawings, in which.

DETAILED DESCRIPTION OF PREFERRED EMBODIMENTS

First Embodiment

Figure 1:
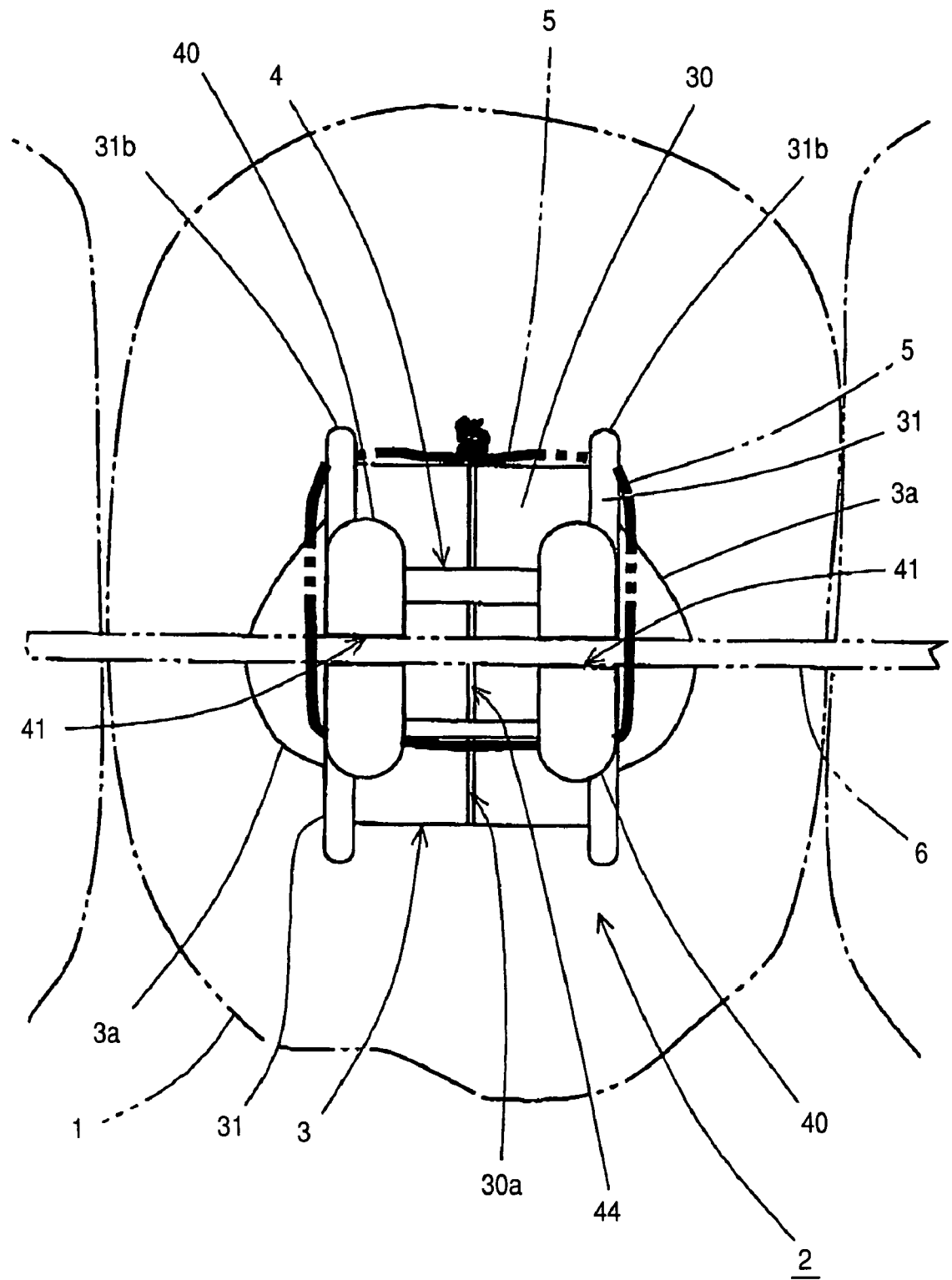
FIG. 1 is a front view showing placement of an orthodontic bracket of a first embodiment according to the present invention to a side surface (or a front surface) of a tooth.
Figure 2:
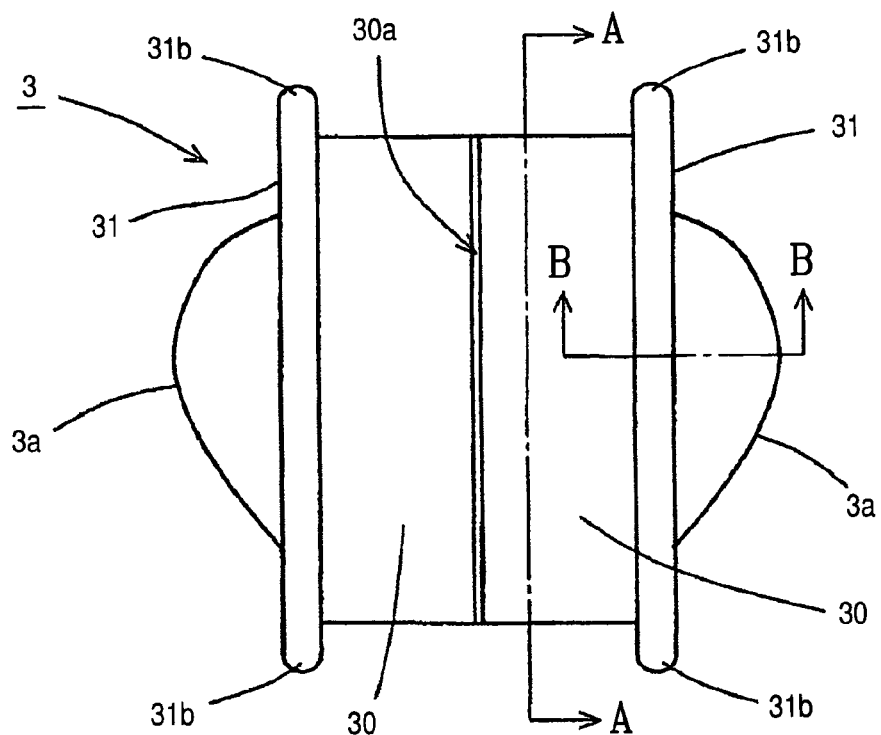
FIG. 2 is a plan view showing a base of the orthodontic bracket in FIG. 1.

Referring to FIG. 1, reference numeral 2 denotes an orthodontic bracket placed on a side surface (or a front surface) of a tooth 1 to be subjected to orthodontic treatment. The tooth 1 in FIG. 1 is shown with its lower end the gingival side (or a root side of the tooth).

Figure 3:
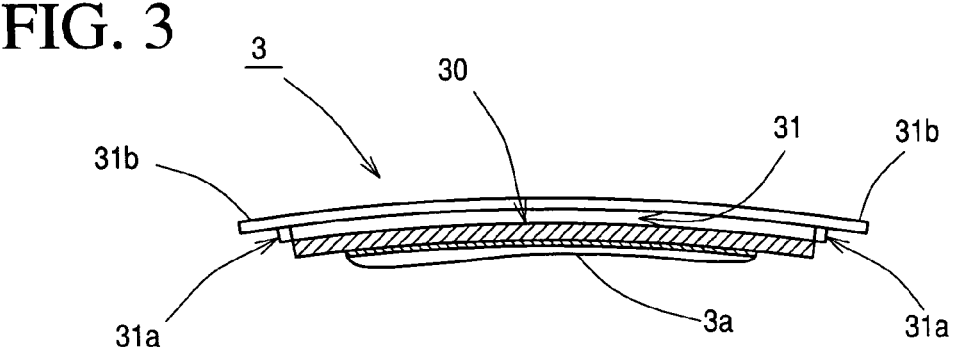
FIG. 3 is a sectional view taken along A-A in FIG. 2.
Figure 4:
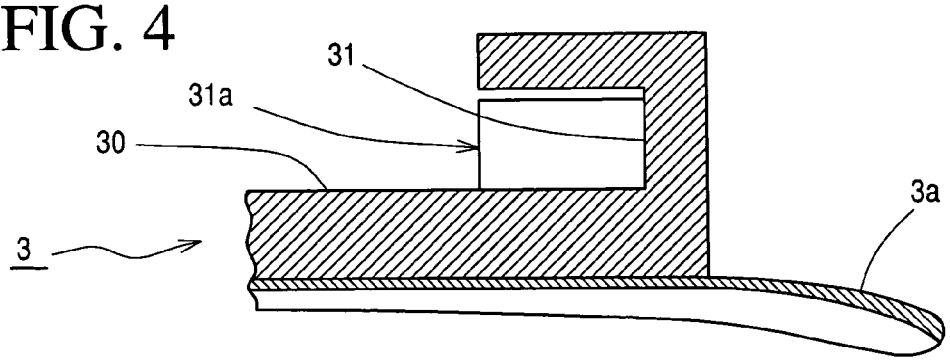
FIG. 4 is a fragmentary enlarged sectional view taken along B-B in FIG. 2.
Figure 5:
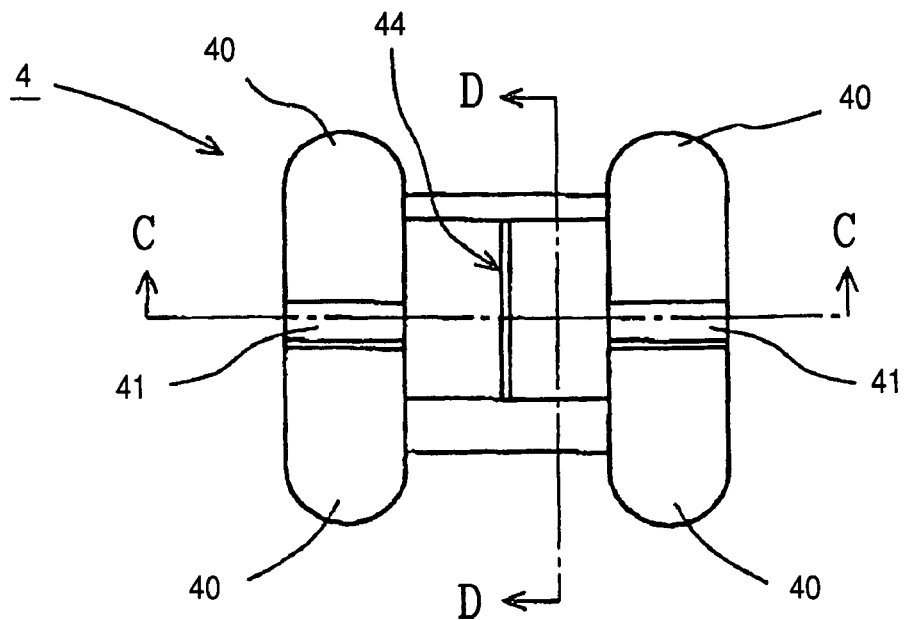
FIG. 5 is a plan view of a bracket body in the orthodontic bracket in FIG. 1.

The orthodontic bracket 2 comprises a bonding plate 3a having a bonding surface matching the curvature of the side surface of the tooth 1, a base 3 (see FIG. 3) having a bottom surface united with the bonding plate 3a and an upper surface (sliding surface) 30 parallel with the side surface of the tooth 1. The base 3 has an approximately rectangular shape with a convex curve conforming to the side surface of the tooth 1. A bracket body 4 is set on the sliding surface 30 of the base 3 in such a way that the bracket body may slide parallel to the longitudinal axis of the tooth 1.

As shown in FIGS. 1 to 7, the base 3 has, on the sliding surface 30, grooved parallel rails 31, 31 which approximately uniformly project from the sliding surface, the rails being adapted to receive the bracket body 4 slidably therein. Each rail 31 has, at its opposite ends, stoppers 31a (see FIGS. 3 and 4) to prevent detachment of the bracket body 4. The sliding surface 30 has, at its widthwise center, a longitudinally extending visible median line 30a.

The bracket body 4 has, on opposing sides of its upper surface, tie-wings 40, 40 protruding therefrom and extending in parallel in a vertical direction. Each tie-wing 40 has, at its longitudinal center, a wire slot 41 arranged approximately orthogonal to the corresponding wing 40 (or approximately orthogonal to the longitudinal axis of the tooth 1).

The orthodontic bracket according to the first embodiment is now described in detail.

While there is no limit on material of the base 3, preferred materials for the base 3 include ceramics such as aluminum oxide and aluminum nitride, epoxy, silicone or like hard resins, stainless steel, titanium alloy, cobalt, chromium allow or other metals. The same materials may also be used for the bonding plate 3a and/or the bracket body 4.

The median line 30a on the sliding surface 30 of the base 3 is formed by coloring or by mechanical notching or grooving. Alternatively, a combination of the mechanical means with the coloring may be used.

Each rail 31 of the base 3 has, at its opposing ends, hooks 31b formed by upper parts of the opposing ends protruding by a prescribed distance longitudinally of the corresponding rail 31. In placement of the bracket body 4 on the sliding surface 30 of the base 3 using a ligature wire 5 to prevent sliding, the ligature wire 5 is put on the upper or lower end hooks 31b.

Figure 7:
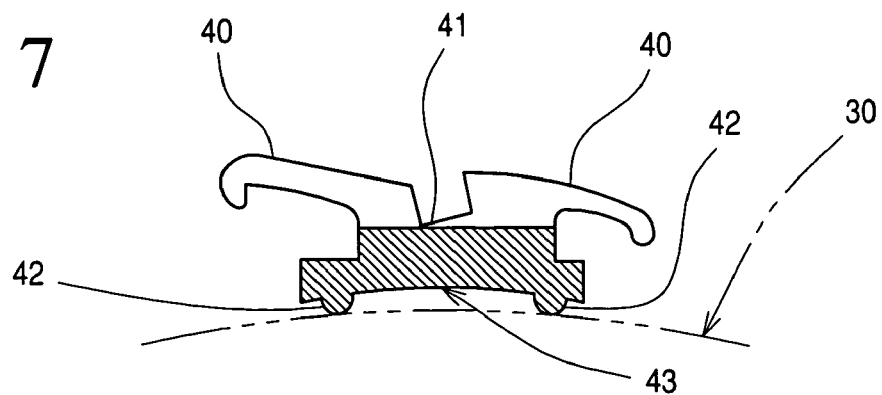
FIG. 7 is a sectional view taken along D-D in FIG. 5.

To prevent damage to the inside of a lip, the tip end of each tie-wing 40 extending vertically from the opposing sides of the bracket body 4 is curved inwardly toward the base as shown in FIG. 7

Figure 6:
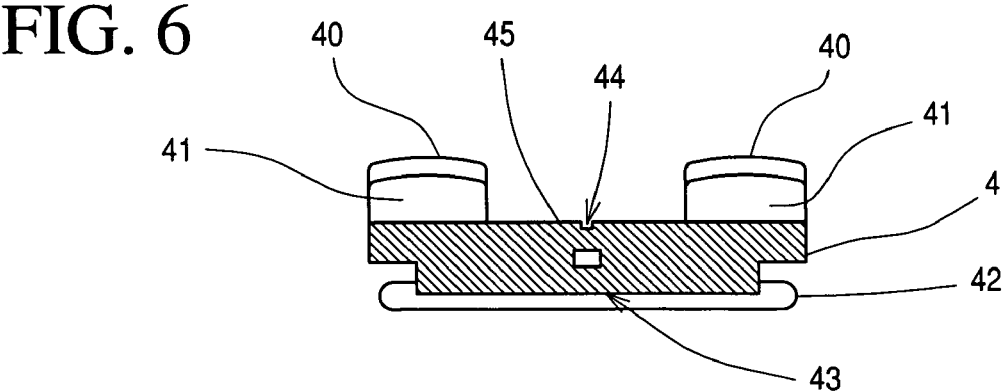
FIG. 6. is a sectional view taken along C-C in FIG. 5.

Preferably, each wire slot 41 of the bracket body 4 has an angular groove-like sectional shape with a gradient in one direction in section (see FIG. 7) to ensure that an arch wire 6 (see FIG. 1) is retained within the corresponding wire slot 41. As shown in FIG. 6, the bracket body has, at its substantially widthwise center, a longitudinally-extending vertical slot 45.

The bracket body 4 has a bottom surface 43 having at least a pair of sliding bars 42, 42 (see FIGS. 6 and 7) spaced in parallel at a prescribed interval in such a way that each sliding bar lies across the bottom surface 43. Each bar 42 has a circular-arc sectional shape and projects from the bottom surface 42. The opposite ends of each sliding bar 42 are slidably received in the rails 31 of the base 3. Each circular-arc sliding bar 42 makes slidable contact with the sliding surface 30 of the base 3 as shown in FIG. 7.

The small distance each sliding bar 42 projects from the bottom surface 43 of the bracket body 4 preferably requires that the bottom surface 43 of the bracket body 4 have a concave-curved shape so as to mate the convex-curved shape of the base 3. This is because forming the bottom surface 43 of the bracket body 4 into the concave-curved shape allows the bottom surface 43 of the bracket body 4 to more successfully match the convex-curved shape of the sliding surface 30 of the base 3 in the case of a small distance of projection of each sliding bar 42 from the bottom surface 43.

Preferably, the upper surface of the bracket body 4 has, at its widthwise center, a median line 44 of the same type as the median line 30a on the sliding surface 30 such that the median lines 44 and 30a are longitudinally in alignment with each other. The median line 44 functions, in cooperation with the median line 30a on the sliding surface 30, as a mark useful in providing alignment of the axis of the base 3, including the bracket body 4, with the longitudinal axis of the tooth 1 when bonding the base 3 (with the bracket body 4 on the sliding surface 30) to the side surface of the tooth 1, so that the alignment of the base with the corresponding tooth may be easily obtained.

Second Embodiment

Figure 8:
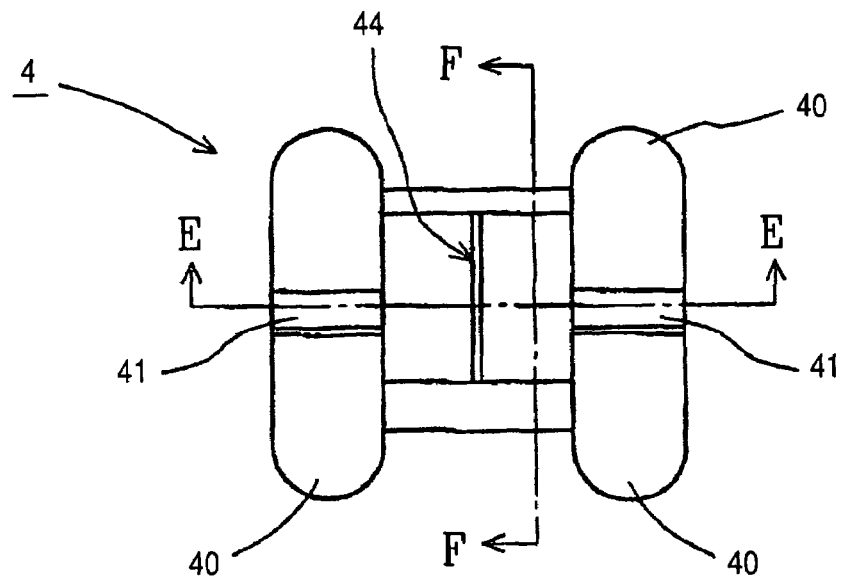
FIG. 8 is a plan view showing the orthodontic bracket of a second embodiment according to the present invention including a modification of the bracket body.
Figure 9:
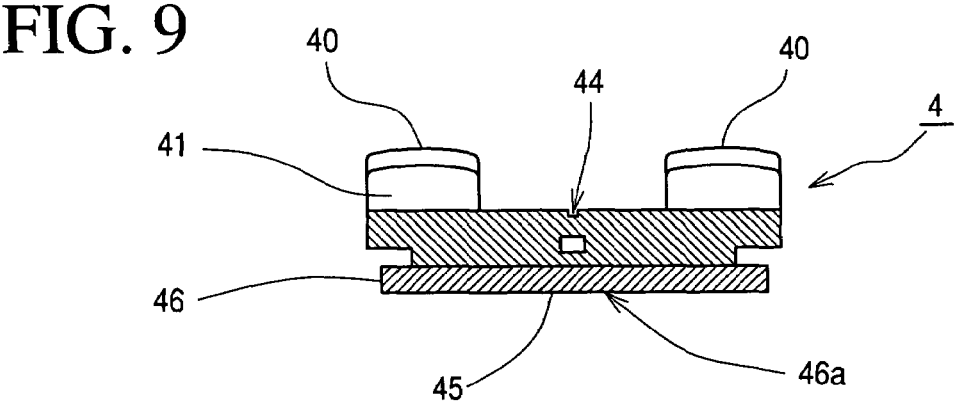
FIG. 9 is a sectional view taken along E-E in FIG. 8.
Figure 10:
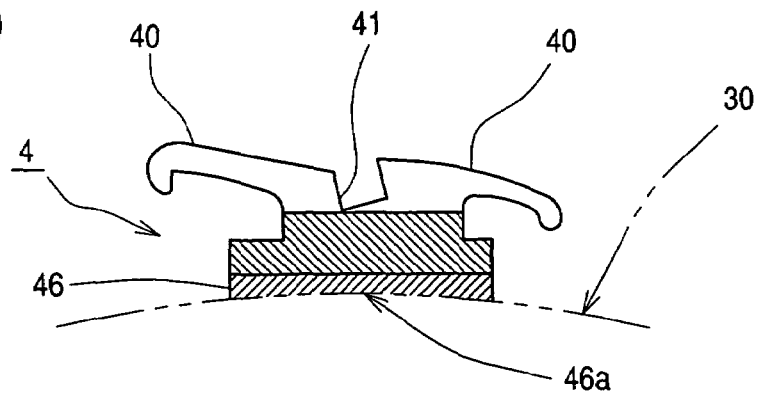
FIG. 10 is a sectional view taken along F-F in FIG. 8.

FIGS. 8 to 10 are views showing the orthodontic bracket of a second embodiment according to the present invention including a modification of the bracket body.

In the second embodiment, there is provided a sliding plate 46 secured to the bottom of the bracket body 4, with the opposite sides of the sliding plate 46 guided by and received in the rails 31 of the base 3. The sliding plate 40 has a bottom surface 40a of a concave-curved shape (see FIG. 10) mating the convex-curved shape of the sliding surface 30 (see FIG. 3) of the base 3. The second embodiment has the sliding plate 46 with a bottom surface 46a having a concave-curved shape as described the above, permitting the base 3 to be so placed on the side surface of the tooth 1 as to better fit the bracket body 4 to the curvature of the side surface of the tooth, in cooperation with the base 3 having the sliding surface 30 of a convex-curved shape.

The orthodontic bracket of the second embodiment is the same as that of the first embodiment in configuration of the base 3, other structure of the bracket body 4 and their operations and effects, so that their description is omitted.

Figure 11:
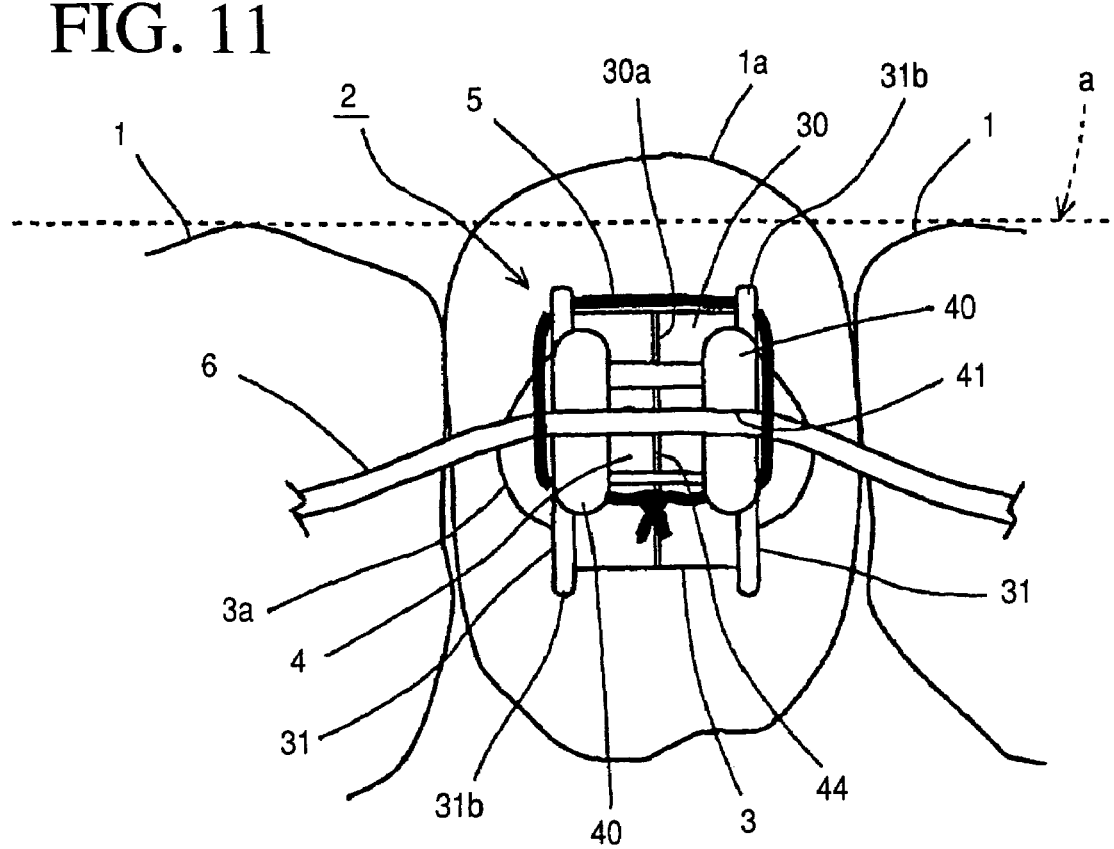
FIG. 11 is a fragmentary front view showing treatment of a protruding tooth using the orthodontic bracket according to the first embodiment.
Figure 12:
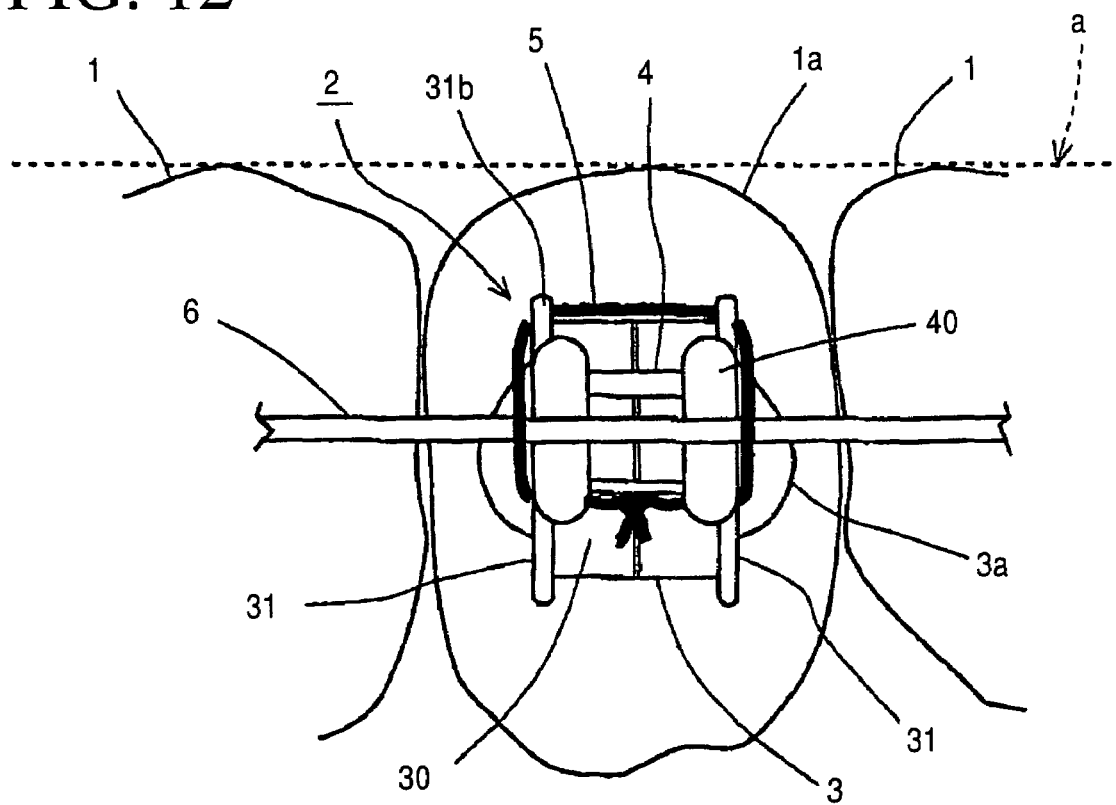
FIG. 12 is a fragmentary front view showing completion of intrusion of the tooth from the state in FIG. 11.

A description is now given, with reference to FIGS. 11 and 12, of treatment of a tooth protruding above other teeth (moving it toward the root side of the tooth), using the orthodontic bracket of the above first embodiment.

In use, the bracket body 4 is first slidably set on the sliding surface 30 of the base 3 by inserting the sliding bars 42, 42 (see FIG. 6) of the bracket body 4 in the respective rails 31 of the base 3.

Each base 3 is then adhesively bonded through its bonding plate to the protruding tooth 1a and each of the other teeth 1 involved in the treatment, with each base 3 positioned with its median line 30a in alignment with the longitudinal axis of the protruding tooth 1a (or a tooth higher than a properly linear occlusal plane a), and also with each bracket body 4 oriented such that each axis (which is the same as the axis of the arch wire 6 described later) of the wire slots 41 is arranged in parallel to the properly linear occlusal plane a (or a normally linear occlusal plane) obtained after intrusion of the protruding tooth 1a.

Next, with the arch wire 6 held in position within the wire slots 41 of each bracket body 4, the ligature wire 5, serving as a fixture, is attached to the hooks 31b located closer to the tooth tip, followed by fastening the bracket body 4 to the base 3 with the ligature wire 5 in cooperation with the arch wire 6 to prevent the bracket body 4 from sliding along the sliding surface 30 of the corresponding base 3. At the same time, the brackets 2 are interconnected.

Afterwards, opposite ends of the arch wire 6 are inserted into respective buccal tubes (not shown) united with more distal teeth, followed by connection of the arch wire to the respective buccal tubes to apply tension to the arch wire 6, and also to press each bracket 2 against the corresponding teeth 1a and 1.

In this stage, each axis of the wire slots 41 (and the arch wire 6) in the bracket body 4 of the orthodontic bracket 2 set on the protruding tooth 1a is arranged closer to the properly linear occlusal plane a than the brackets on the other teeth 1, offset toward the tooth tip by a distance required for intrusion or somewhat exceeding the required distance.

With this arrangement, the protruding tooth 1a requiring intrusion gradually shifts toward the normally linear occlusal plane a (obtained after intrusion).

When the intrusion of the protruding tooth 1a is advanced to a stage necessitating a change in the setting of the bracket position on the protruding tooth 1a, repositioning of the bracket body 4 is performed by shifting the bracket body 4 along the sliding surface 30 of the base 3 by a required distance in the vertical direction through the process of loosening or detaching the ligature wire 6, while loosening the arch wire 6. Then, with the repositioned bracket body 4 re-fixed to the sliding surface 30 of the base 3 by ligature wire 6 to prevent sliding, the opposite ends of the arch wire 6 are reinserted into the respective buccal tubes, followed by reconnection of the arch wire to the respective buccal tubes to reapply tension to the arch wire 6.

Thus, there is no need to reset the bracket body 4 and/or the arch wire 6 every time the intrusion of tooth 1a is advanced to a stage necessitating a change in setting of the bracket position on the tooth 1a. Accordingly, the orthodontic bracket of the present invention enables the orthodontic treatment to be performed in a shorter period of time, and also relieves the burden on the patient.

Further, the orthodontic bracket of the present invention has a base 3 of a convex-curved shape in accordance with the vertical direction of the tooth, and the bracket body 4 has the concave-curved bottom surface 43 mating with the convex-curved base 3, permitting more successful matching of the convex-curved base 3 to the tooth side surface to be obtained, and also permitting the orientation of the bracket body 4 set on the sliding surface of the convex-curved base 3 to better match the tooth side surface.

When the tip of the protruding tooth 1a comes into alignment with the normally linear occlusal plane a, and hence, parallel arrangement of the axis of the arch wire 6 with the normally linear occlusal plane a is obtained, the intrusion of the protruding tooth 1a is completed.

Figure 13:
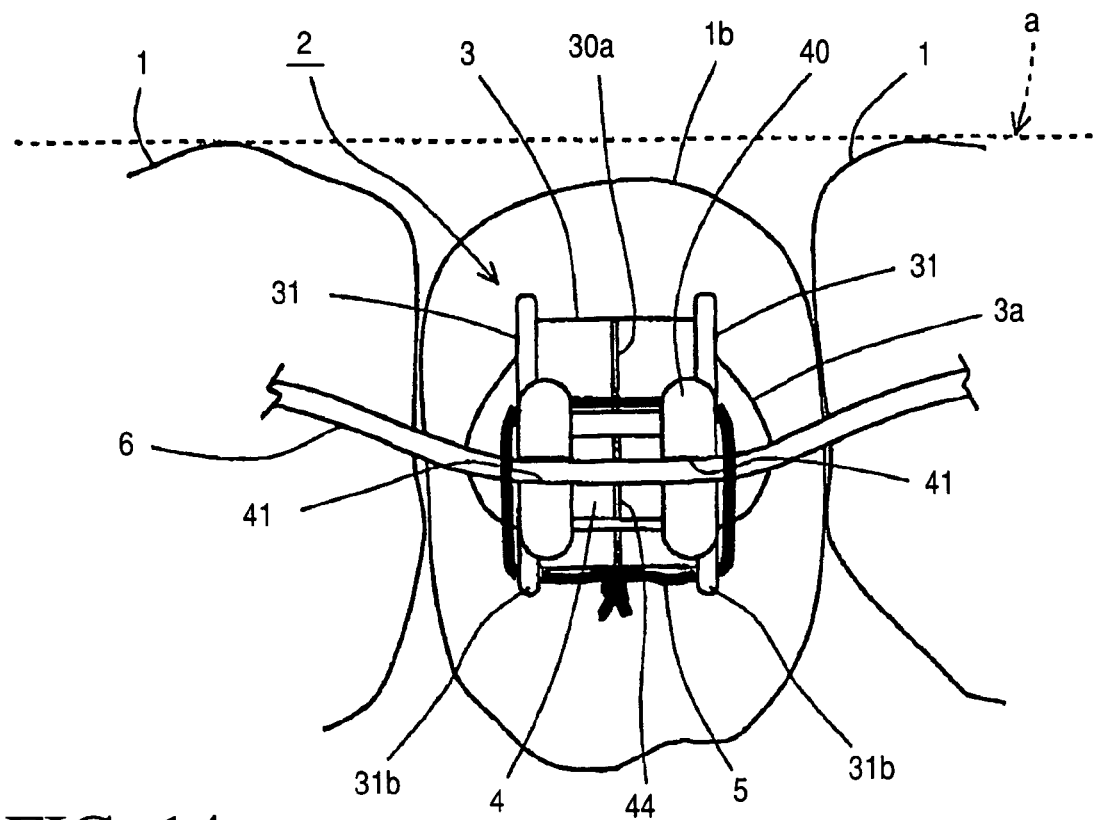
FIG. 13 is a fragmentary front view showing treatment of an intruding tooth using the orthodontic bracket according to the first embodiment.

For raising a tooth 1b having its upper surface below the normally linear occlusal plane a, i.e. back toward the root side of the tooth, attachment of the orthodontic bracket 2 to the tooth 1b to be raised is as shown in FIG. 13. Specifically, the ligature wire 5 is put on the hooks 31b located closer to the root of the tooth. Further, each axis of the arch wire 6 and the wire slots 41 of the bracket 2 set on the tooth 1b is arranged more distant from the properly linear occlusal plane than on the other teeth 1, toward the root side of the tooth by a distance required for leveling or somewhat exceeding the required distance.

Figure 14:
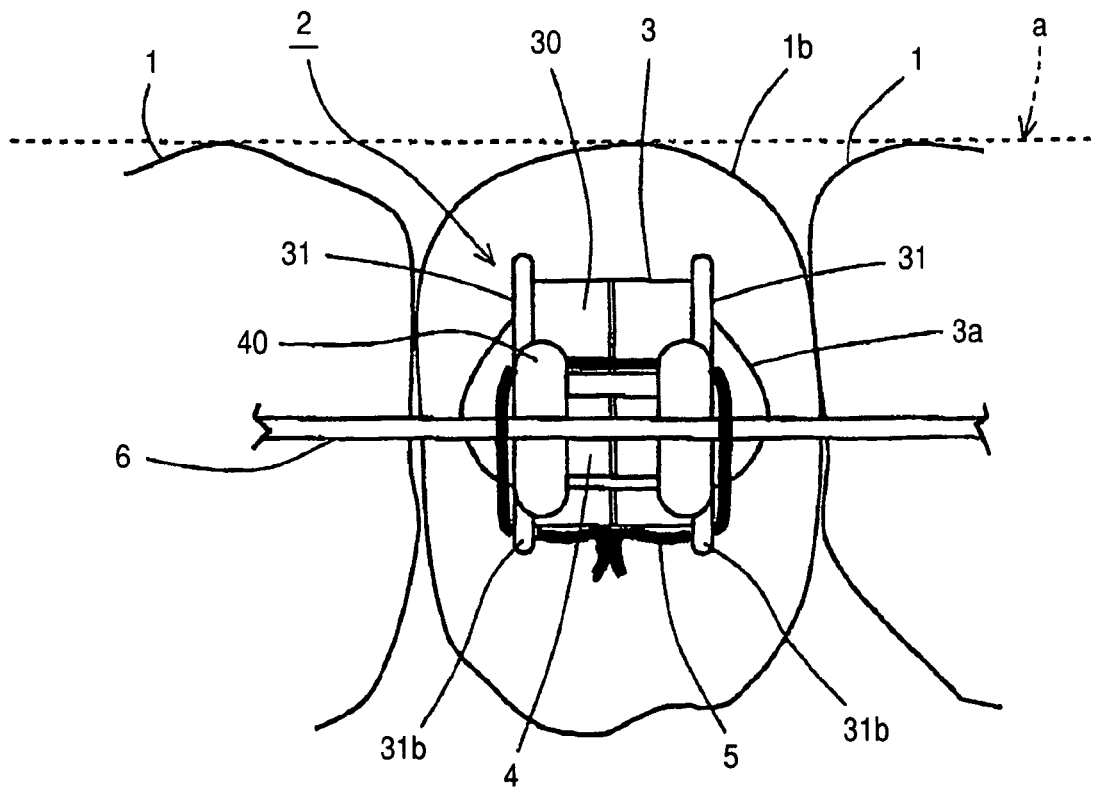
FIG. 14 is a fragmentary front view showing a completion of extrusion of the tooth from the state in FIG. 13.

A completed state of leveling of the tooth 1b is as shown in FIG. 14. Details of other procedures taken to attach each orthodontic bracket to the tooth and/or other operations and effects of each orthodontic bracket are the same as those previously described with reference to FIGS. 11 and 12.

For the orthodontic treatments other than raising or lowering a tooth, that is, distal movement (or movement from an incisor toward molars) or mesial movement (or movement from a molar side toward incisors) of the tooth to be orthodontically treated, attachment of the orthodontic bracket 2 to a tooth 1 to be corrected is as shown in FIG. 1. Procedures taken to attach each orthodontic bracket in this case are substantially the same as the previously described procedures.

The previously described procedures may be also applied to the orthodontic treatment using the orthodontic bracket 2 according to the second embodiment.

The bracket is usually bonded in an accurate bracket position with a jig or a gauge. A fixation apparatus for fixing the bracket body to a specific location on the base is a jig or gauge like the conventional. The fixation apparatus is a detachable type. Thus, the fixation apparatus may be detached as needed, or used as usual by resetting the fixation apparatus.

Third Embodiment

Figure 15:
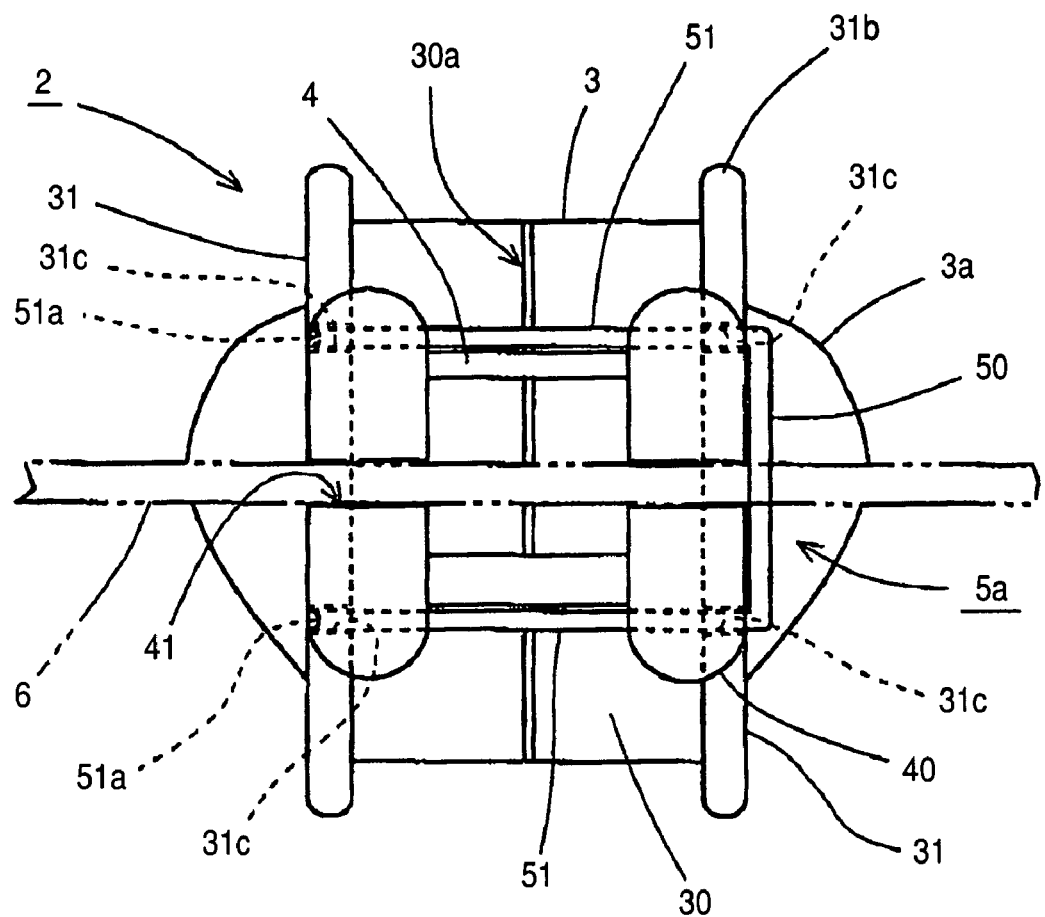
FIG. 15 is a schematic front view showing the orthodontic bracket of a third embodiment according to the present invention.
Figure 16:
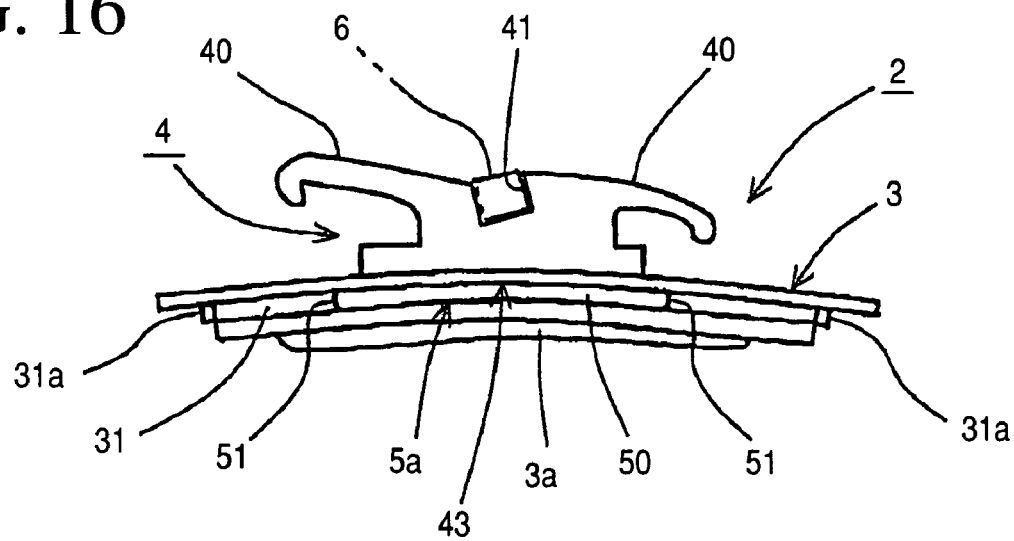
FIG. 16 is a right side view of the orthodontic bracket in FIG. 15.

FIGS. 15 and 16 show a third embodiment of the orthodontic bracket in which a fixture is substituted for the ligature wire. It is to be noted that configurations and/or arrangements of the base 3 and the bracket body 4 in the third embodiment, except for a fixture-related portion, are the same as those in the second embodiment, and hence, their description is omitted. The same is also true for fourth and fifth embodiments described later.

The fixture 5a is a member which is approximately U-like shaped in plan view and composed of a basal part 50 arranged in parallel with and outside of one rail 31 with the fixture attached to the base 3, and a pair of linear legs 51, 51 extending in one direction from the opposite ends of the basal part 50, the linear legs being adaptable to hold the bracket body 4 set on the sliding surface 30 of the base 3 from the upper and lower sides of the bracket body. Here, the rails 31, 31 of the base 3 have, in four locations, holes 31c, 31c through which the respective linear legs 51 of the fixture 5a extend from one side of the base 3 to the other side at approximately right angles to the rails 31.

After insertion of the linear legs 51, 51 of the fixture 5a through the corresponding holes 31c from one side of the base 3 (see FIG. 15), a lower part of the bracket body 4 is inserted into a space enclosed by the rails 31 and the linear legs 51 to prevent the bracket body 4 from sliding on surface 30 of the base 3.

The third embodiment allows the arch wire 6 to be placed in the wire slots 41 of the bracket body 4 after mounting of the bracket body 4 on the base 3 in the above manner (which also applies to the fourth and fifth embodiments).

It is to be noted that each linear leg 51 preferably has, in its distal end, a depression 51a which receives dental equipment such as an explorer (not shown) having a tip end in the form of a hook-like pin, for instance, for removing legs 51 from holes 31c for easy detachment of the fixture 5a. More specifically, detachment of the fixture 5a takes advantage of a clearance left between one rail 31 and the base 50 created by pushing out the linear legs 51 by a small distance by pressing a pin tip into contact with the depression 51a.

Fourth Embodiment

Figure 17:
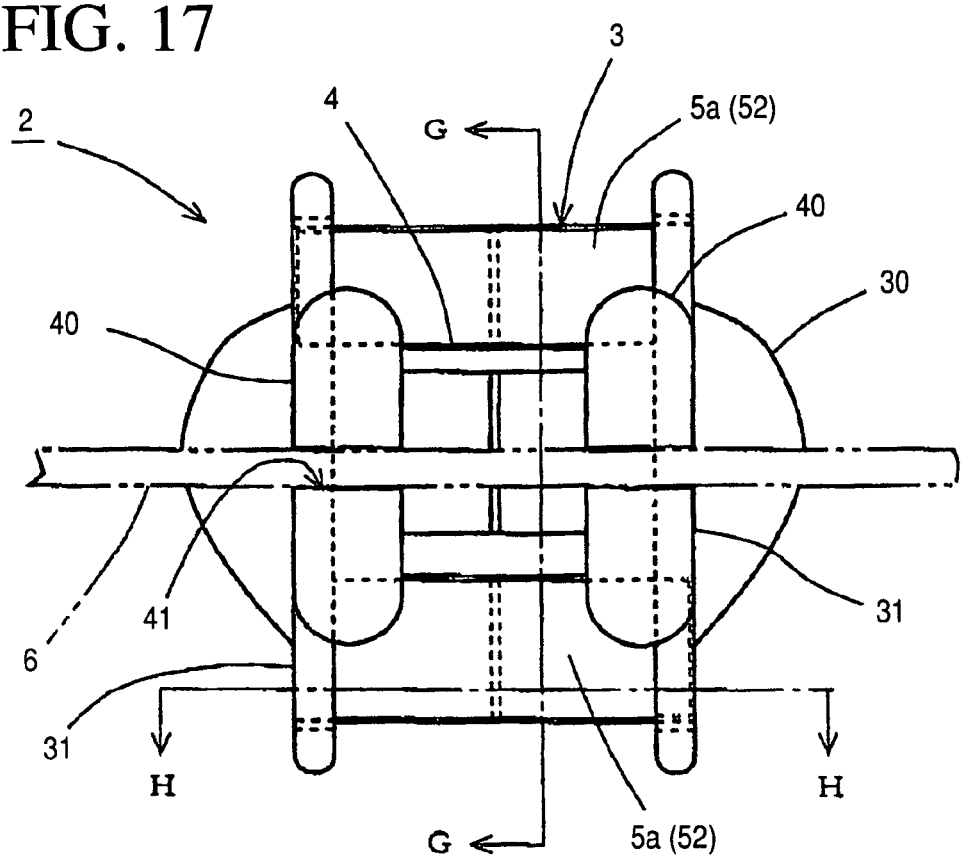
FIG. 17 is a schematic front view showing the orthodontic bracket of a fourth embodiment according to the present invention.
Figure 18:
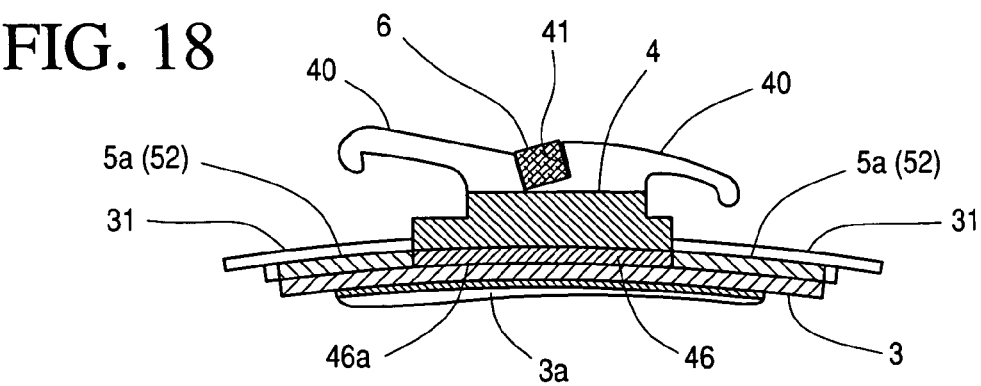
FIG. 18 is a sectional view taken along a line G-G in FIG. 17.
Figure 19:
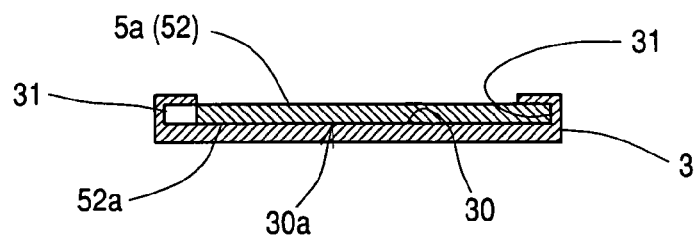
FIG. 19 is a sectional view taken along a line H-H in FIG. 17.

FIGS. 17 to 19 show a fourth embodiment of the orthodontic bracket in which a fixture of a different type is substituted for the ligature wire.

The fixture 5a is composed of at least a pair of spacer members 52, 52 each having opposing ends inserted in the grooves of the rails of the base 3 with spacer member sliding restricted by the stoppers 31a of the rails 30. Thus, the spacer members hold the bracket body 4 set on the sliding surface 30 of the base 3 from the upper and lower sides of the bracket body, with the spacer members placed in the respective rails.

Each spacer member 52 has a plate-like form, and one end of each spacer member 52 to be fit in one rail 31 is in the form of a wedge having a thickness gradually decreasing approaching its tip end as shown in FIG. 19. Setting of the spacer members 52 on the base 3 in FIGS. 17 and 18 involves inserting the one wedge-like end of each spacer member 52 into one rail 31 from the upper side of the base 3, bringing the inserted spacer member 52 into contact with the sliding surface 30 as shown in FIG. 19, followed by pressing in the other end of the inserted spacer member a small distance toward the other rail 31.

With the fixture 5a set on the sliding surface 30 of the base 3 as shown in FIG. 17, insertion of the lower side of the bracket body 4 into the space enclosed by the rails 31 and the spacer members 52 allows the bracket body 4 to be attached to the sliding surface 30 of the base 3 while held against sliding.

At least one side of each spacer member 52 preferably has, on its back surface, a groove-like notch 52a (see FIG. 19). With this arrangement, use of dental equipment such as an explorer (not shown) having a tip end in the form of the hook-like pin, allows easy detachment of the spacer members from the base 3 by hooking the pin of the explorer in the notch 52a.

Fifth Embodiment

Figure 20:
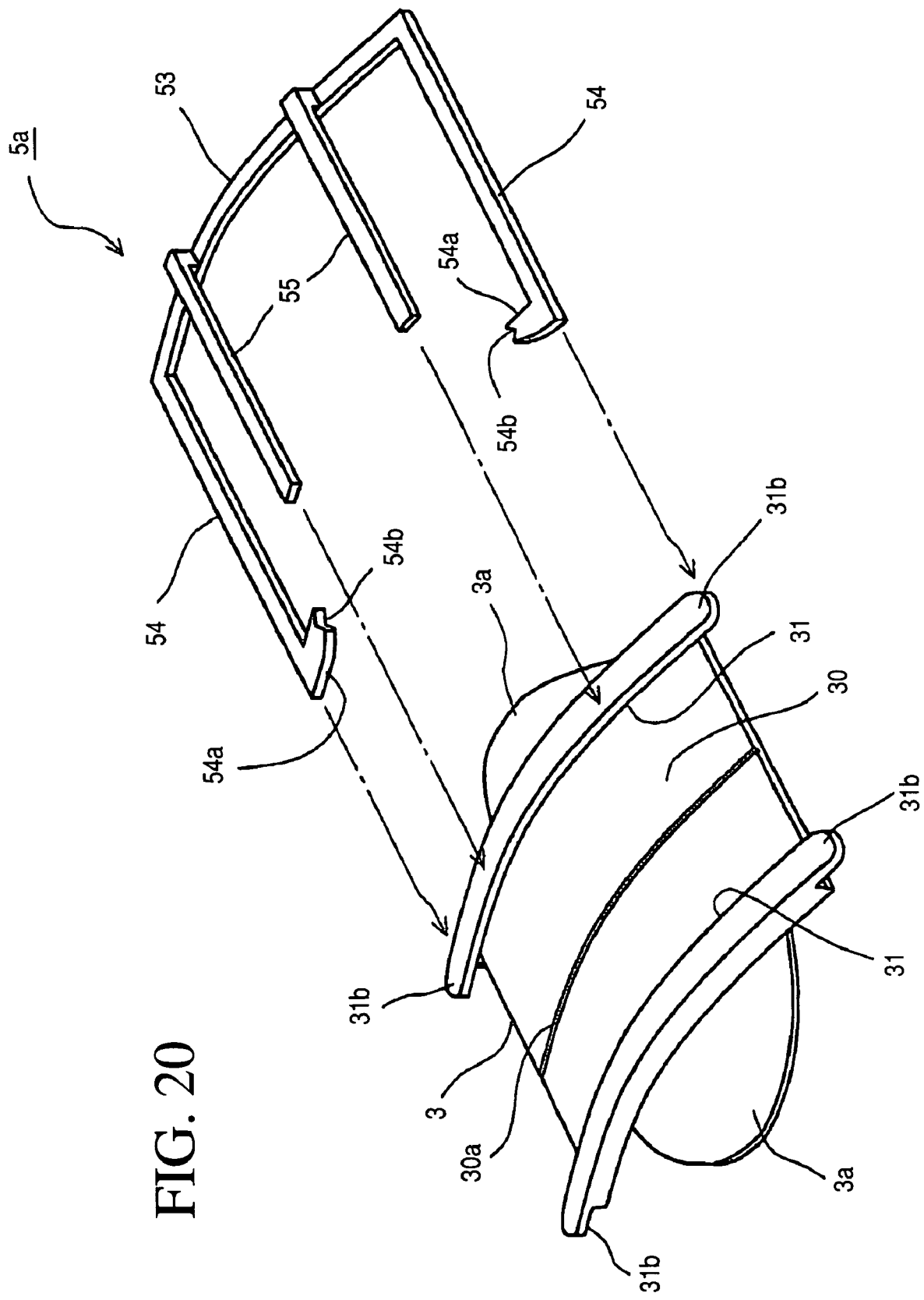
FIG. 20 is a fragmentary exploded perspective view showing the relationship between the base and a fixture in the orthodontic bracket of a fifth embodiment according to the present invention.
Figure 21:
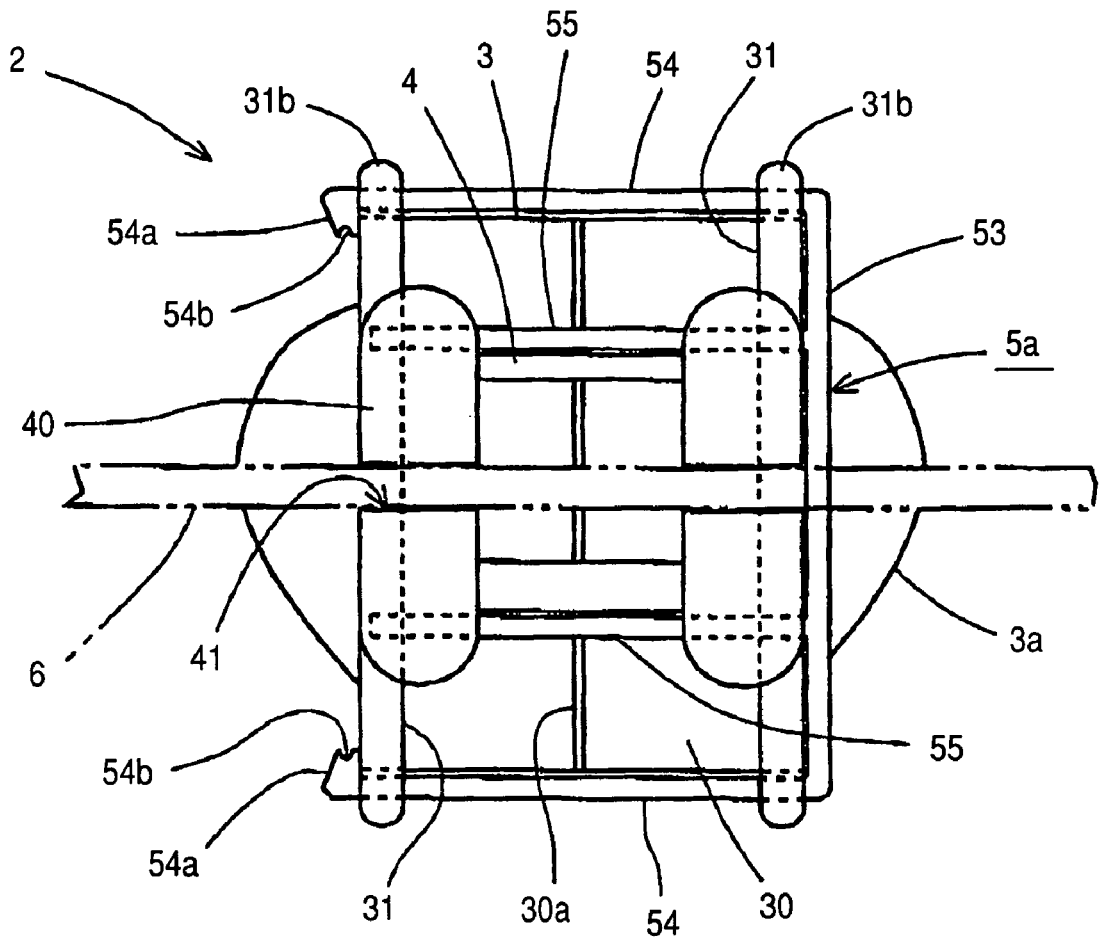
FIG. 21 is a front view showing the orthodontic bracket of the fifth embodiment, which includes the base and the fixture in FIG. 20.
Figure 22:
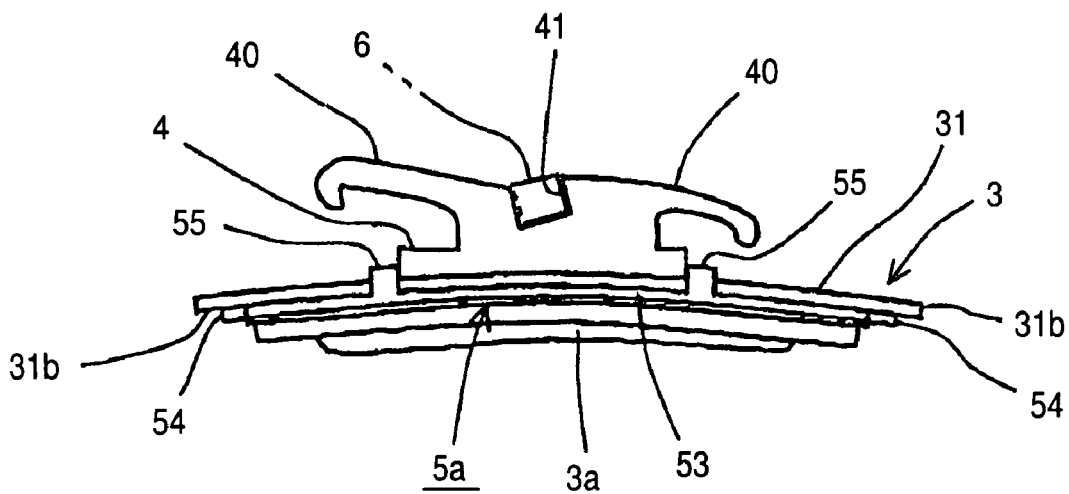
FIG. 22 is a right side view of the orthodontic bracket in FIG. 21.

FIGS. 20 to 22 show a fifth embodiment of the orthodontic bracket wherein a different type of fixture is substituted for the ligature wire.

The fixture 5a is an elastic metal member having a basal part 53 arranged in parallel with rails 31 of the base 3, with the bracket body 4 set on the sliding surface 30 of the base 3.

The basal part 53 has, depending from its opposing ends, a pair of first arms 54, 54 extending from and approximately orthogonal to one side of the basal part 53 for fitting with the rails by sliding under the hooks 31b of rails 31. Each of the first arms has at its tip end, a hook 54a to be hooked around the corresponding ends of the far rail 31.

The basal part 53 has, closer to its center, a pair of second arms 55, 55 integral with, extending from and approximately orthogonal to one side of the basal part so as to cross over the upper surface of each rail 31 of the base 3. Thus, the second arms are adapted to hold the bracket body 4 set on the sliding surface 30 of the base 3 from the upper and lower sides of the bracket body.

Attachment of the fixture 5a to the base 3 as shown in FIG. 21 allows each rail 31 of the base 3 to be held at both the upper and lower surfaces by elastic force of the pairs of first and second arms 54 and 55. Then insertion of the lower side of the bracket body 4 into the space enclosed by the second arms 55 and the rails 31 allows the bracket body 4 to be attached on the sliding surface 30 of the base 3 and held against sliding.

The hook 54a in each first arm 54 has, at its tip end, a concave-shaped notch 54a, 54b, so that dental equipment such as an explorer (not shown) having a tip end in the form of the hook-like pin, can be used for detaching the fixture 5a from the base 3 by hooking the pin of the explorer in the concave-shaped notch 54b.

The orthodontic bracket of the present invention is also applicable to orthodontic treatments according to an edgewise or tip edge technique.

What is claimed is:

1. An orthodontic bracket for placement on a side surface of a tooth for correcting irregularities in alignment of teeth, comprising:
    a bonding plate having a bonding surface matching a contour of a side surface of a tooth;
    a base having a bottom surface united with said bonding plate and an upper surface serving as a sliding surface parallel to the side surface of the tooth and having an approximately rectangular, convex-curved shape; and
    a bracket body set on said sliding surface of said base for vertical sliding movement relative to said base along a longitudinal axis of the tooth;
    wherein said base has, at opposing sides of said sliding surface, grooved parallel rails slidably holding opposing portions of said bracket body, said opposing portions being fully seated within said grooved parallel rails for adjustment of the vertical position of said bracket body on the longitudinal axis relative to the base, each rail having, at opposing ends, stoppers to prevent detachment of said bracket body, said sliding surface having, at its widthwise center, a longitudinally-extending visible median line;
    wherein said bracket body has, on its upper surface, opposite said base, wire slots arranged approximately orthogonal to the longitudinal axis of the tooth;
    wherein each rail of said base has, at its opposing ends, hooks formed as parts of said opposing ends protruding longitudinally of the rail; and
    wherein the orthodontic bracket further comprises a fixture for attaching said bracket body to the sliding surface of said base to prevent the bracket body from sliding vertically along the longitudinal axis on said sliding surface.

2. The orthodontic bracket according to claim 1, wherein said bracket body has a bottom surface facing the sliding surface of said base, at least a pair of sliding bars, each sliding bar having a circular arc sectional shape and extending across and protruding from said bottom surface into contact with said sliding surface, and wherein each sliding bar has opposing free ends, serving as said opposing portions, which are guided by and received in the rails of said base.

3. The orthodontic bracket according to claim 2, wherein said bracket body has a concave-curved bottom surface mating with the convex-curved shape of said base.

4. The orthodontic bracket according to claim 1, wherein said bracket body has, on its bottom, a sliding plate with opposing ends, serving as said opposing portions, being guided by and received in the rails of said base, and wherein said sliding plate has a concave-curved bottom surface mating the convex-curved shape of said base.

5. The orthodontic bracket according to claim 1, wherein said fixture is a ligature wire engaged by said hooks.

* * * * *